(12) United States Patent
Seneschal et al.

(10) Patent No.: US 7,704,903 B2
(45) Date of Patent: Apr. 27, 2010

(54) ANTIMICROBIAL PHOSPHATE GLASS WITH ADAPTED REFRACTIVE INDEX

(75) Inventors: Karine Seneschal, Mainz (DE); José Zimmer, Ingelheim (DE); Jörg Hinrich Fechner, Mainz (DE); Bianca Schreder, Frankfurt (DE)

(73) Assignee: Schott AG, Mainz (DE)

( * ) Notice: Subject to any disclaimer, the term of this patent is extended or adjusted under 35 U.S.C. 154(b) by 1447 days.

(21) Appl. No.: 11/076,113

(22) Filed: Mar. 8, 2005

(65) Prior Publication Data

US 2005/0233888 A1   Oct. 20, 2005

(30) Foreign Application Priority Data

Mar. 8, 2004   (DE) ................. 10 2004 011 520

(51) Int. Cl.
*C03C 3/16* (2006.01)
*C03C 3/21* (2006.01)
*C03C 3/19* (2006.01)
*C03C 3/17* (2006.01)

(52) U.S. Cl. ............... 501/45; 501/46; 501/47; 501/48; 501/2; 501/4; 501/5; 501/10

(58) Field of Classification Search ............. 501/45, 501/46, 47, 48, 2, 4, 5, 10
See application file for complete search history.

(56) References Cited

U.S. PATENT DOCUMENTS

| | | | | |
|---|---|---|---|---|
| 3,785,835 | A * | 1/1974 | Izumitani et al. | 501/47 |
| 3,798,041 | A * | 3/1974 | Izumitani et al. | 501/47 |
| 5,022,921 | A * | 6/1991 | Aitken | 106/38.9 |
| 5,196,381 | A * | 3/1993 | Hu et al. | 501/10 |
| 5,234,871 | A * | 8/1993 | Krashkevich | 501/73 |
| 5,290,544 | A | 3/1994 | Shimono et al. | 424/63 |
| 6,143,318 | A | 11/2000 | Gilchrist et al. | 424/446 |
| 6,831,028 | B1 * | 12/2004 | Ishii et al. | 501/33 |

FOREIGN PATENT DOCUMENTS

| | | |
|---|---|---|
| EP | 141580 | 10/1984 |
| JP | 62128943 A * | 6/1987 |
| JP | 62153144 A * | 7/1987 |
| JP | 92 338129 | 11/1992 |
| JP | 96 048539 | 2/1996 |
| JP | 2000 327369 | 11/2000 |
| JP | 2001 247333 | 9/2001 |
| JP | 2001 247335 | 9/2001 |
| JP | 2001 247336 | 9/2001 |
| JP | 2001 247337 | 9/2001 |
| JP | 2002 012442 | 1/2002 |
| WO | WO 02/28792 * | 4/2002 |
| WO | PCT/EP03/000559 | 1/2003 |

OTHER PUBLICATIONS

Speier et al., "Destruction of Mricoorganisms by Contact with Solid Surfaces," Journal of Colloid and Interface Science, vol. 89, No. 1, pp. 68-76, Sep. 1982.

Kenawy et al., "Biologically active polymers: synthesis and antimicrobial activity of modified glycidyl methacrylate polymers having a quaternary ammonium and phosphonium groups," Journal of Controlled Release 50, pp. 145-152, 1998.

Gottenbos et al, "Initial adhesion and surface growth of *Pseudomonas aeruginosa* on negatively and positively charged poly(methacrylates)," Journal of Materials Science: Materials in Medicine 10, pp. 853-855, 1999.

* cited by examiner

*Primary Examiner*—Anthony J Green
*Assistant Examiner*—Elizabeth A Bolden
(74) *Attorney, Agent, or Firm*—Ohlandt, Greeley, Ruggiero & Perle, L.L.P.

(57) ABSTRACT

The invention provides an antimicrobial phosphate glass composition including, in weight percent based on oxide: greater than 45 to 90 of $P_2O_5$, 0 to 60 of $B_2O_3$, 0 to 40 of $SiO_2$, 0 to 20 weight percent of $Al_2O_3$, 0 to 30 of $SO_3$, 0 to 0.1 of $Li_2O$, 0 to 0.1 of $Na_2O$, 0 to 0.1 of $K_2O$, 0 to 40 of CaO, 0 to 40 of MgO, 0 to 15 of SrO, 0 to 40 of BaO, 0 to 40 of ZnO, 0 to 5 of $Ag_2O$, 0 to 15 of CuO, 0 to 10 of $Cr_2O_3$, 0 to 10 of I—, 0 to 10 of $TeO_2$, 0 to 10 of $GeO_2$, 0 to 10 of $TiO_2$, 0 to 10 of $ZrO_2$, 0 to 10 of $La_2O_3$, 0 to 5 of $Nb_2O_5$, 0 to 5 of $CeO_2$, 0 to 5 of $Fe_2O_3$, 0 to 5 of $WO_3$, 0 to 5 of $Bi_2O_3$, and 0 to 5 of $MoO_3$.

27 Claims, 1 Drawing Sheet

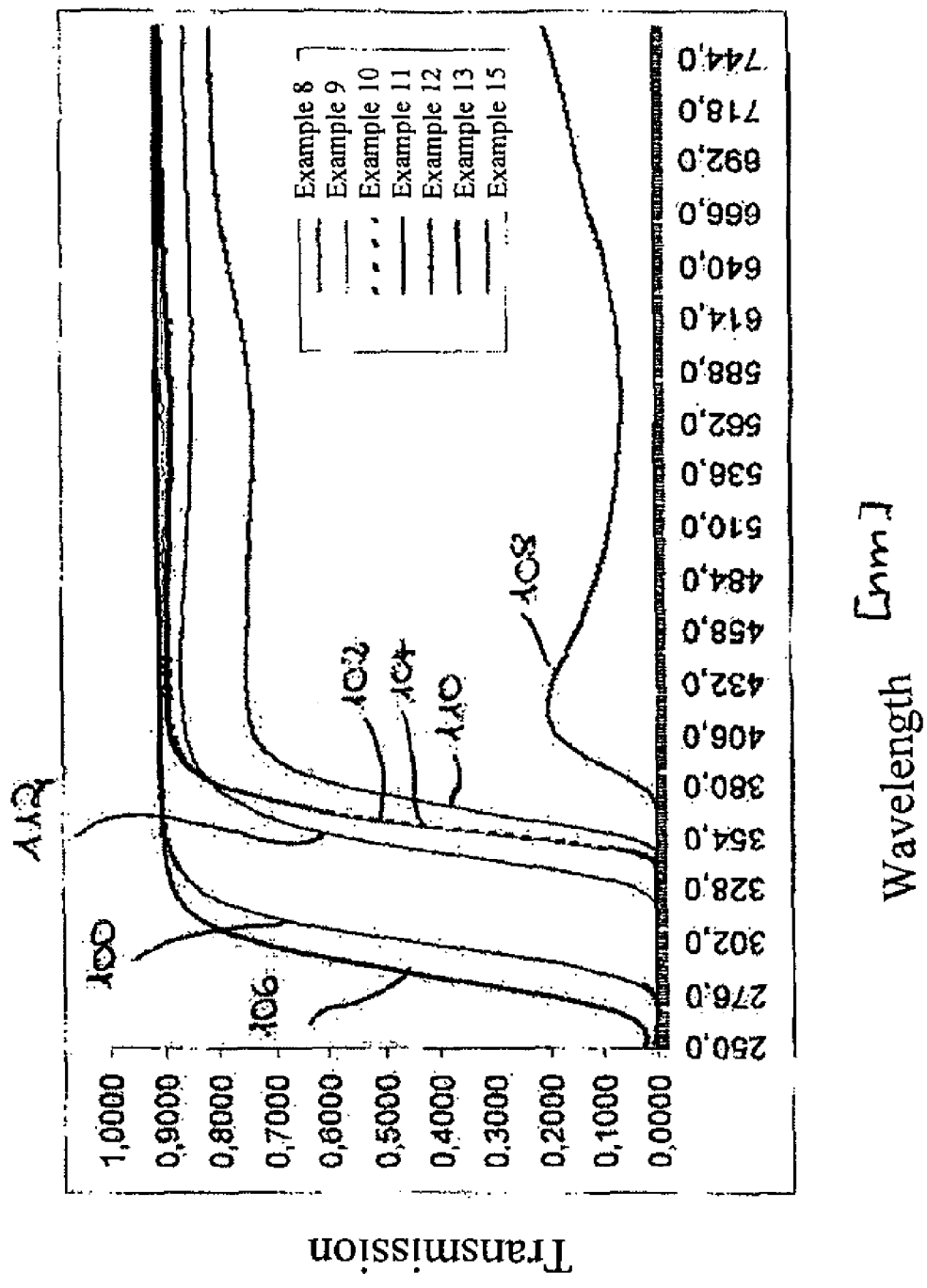
Figure 1 – Transmission Spectra

ANTIMICROBIAL PHOSPHATE GLASS WITH ADAPTED REFRACTIVE INDEX

The invention refers to antimicrobial glasses, glass ceramics, particularly glass powders and glass ceramic powders, glass fibers, glass granulates, and glass beads based on essentially alkali-free phosphate glasses that have an antimicrobial action.

BACKGROUND OF THE INVENTION

1. Field of the Invention

Described in U.S. Pat. No. 5,290,544 are water-soluble glasses for application in cosmetic products with very small $SiO_2$ and very high $B_2O_3$ or high $P_2O_5$ contents. The glasses have silver concentrations of <0.5 wt %. These glasses have an extremely low hydrolytic resistance and have the drawback of completely dissolving in water. The antibacterial action in these glasses is effected by the liberated Ag and/or Cu ions.

2. Background of the Invention

Described in U.S. Pat. No. 6,143,318 are silver-containing phosphate glasses, which, as antimicrobial material for the treatment of wound infection, use combinations of Cu, Ag, and Zn. The drawback of these glasses is their low hydrolytic resistance, which is expressed in the fact that the glasses are completely water-soluble. These glasses contain no $Al_2O_3$ and/or $SiO_2$, which serve to adjust the hydrolytic resistance. Furthermore, the concentration of $Na_2O$ of 34 mol % is very high. This is responsible for the fact that the reactivity of the glass is very high and that it dissolves completely relatively rapidly.

Phosphate or borophosphate glasses that have no titanium have also become known from the following documents:

JP A 2001 247,333

JP A 2001 247,335

JP A 2001 247,336

JP A 2001 247,337

JP A 92 338,129

JP A 2001 247,333 describes a glass fiber that is furnished antimicrobially with $Ag_2O$ in a later process step.

JP A 2001 247,336, JP A 2001 247,335 also describe a glass composition that is furnished antimicrobially with $Ag_2O$ in a subsequent process step.

The subsequent addition of $Ag_2O$ leads to the fact that composite materials are formed, in which silver or silver agglomerates are deposited on the surface of the glass phase, so that a homogeneous distribution of the silver is not present.

Described in JP 92 338,129 is a soluble glass that may be free of alkalis and aluminum is described. This glass achieves its antimicrobial action through the addition of silver.

Glass compositions that contain $TiO_2$ are known from the following documents:

JP A 2002 012,442

JP A 96 048,539

EP A 141,580

JP A 2000 327,369

The glasses known from the documents EP A 141,580 and JP A 2000 327,369 have a phosphorus content that is less than 45 wt %.

The glasses known from the documents JP A 2002 012,442 and JP A 96 048,539 have an alkali content that is greater than 0.39 wt %, which, for use in polymers, such as, for example, polycarbonate, has the drawback that such alkali concentrations can lead to chain rupture and thus the polymer degenerates. In addition, as a rule, there arises an undesired discoloration of the polymers.

BRIEF SUMMARY OF THE INVENTION

The object of the invention is to provide an antimicrobial glass composition to which other substances, such as, for example, polymers can be added, it being possible to adjust the refractive index of the glass composition in order to make possible substances, particularly polymers, that are as transparent as possible, by means of refractive index adjustment. Preferably, in addition, the UV edge or the transmission of the glasses should be adjustable. The glasses should have an antimicrobial action with relatively high chemical resistance as well as high reactivity. In particular, the glass composition should be highly antimicrobial and suitable as an additive substance also for polymers, such as, for example, polycarbonates. Furthermore, no yellowing of the polymers during the manufacturing process or else during their use as well as no detrimental mechanical effects, such as, for example, embrittlement, should arise. It is especially advantageous when the chemical resistance can be adjusted as well.

In accordance with the invention, the problem is solved by the following, antimicrobial glass compositions (in wt % based on oxide), which can also be a basis for glass ceramics:

| | |
|---|---|
| $P_2O_5$ | >45-90 wt % |
| $B_2O_3$ | 0-60 wt % |
| $SiO_2$ | 0-40 wt % |
| $Al_2O_3$ | 0-20 wt % |
| $SO_3$ | 0-30 wt % |
| $Li_2O$ | 0-0.1 wt % |
| $Na_2O$ | 0-0.1 wt % |
| $K_2O$ | 0-0.1 wt % |
| CaO | 0-40 wt % |
| MgO | 0-40 wt % |
| SrO | 0-15 wt % |
| BaO | 0-40 wt % |
| ZnO | 0-40 wt % |
| $Ag_2O$ | 0-5 wt % |
| CuO | 0-15 wt % |
| $Cr_2O_3$ | 0-10 wt % |
| I— | 0-10 wt % |
| $TeO_2$ | 0-10 wt % |
| $GeO_2$ | 0-10 wt % |
| $TiO_2$ | 0-10 wt % |
| $ZrO_2$ | 0-10 wt % |
| $La_2O_3$ | 0-10 wt % |
| $Nb_2O_3$ | 0-5 wt % |
| $CeO_2$ | 0-5 wt % |
| $Fe_2O_3$ | 0-5 wt % |
| $WO_3$ | 0-5 wt % |
| $Bi_2O_3$ | 0-5 wt % |
| $MoO_3$ | 0-5 wt % | wherein the sum formed from $TiO_2+ZrO_2+BaO+La_2O_3+Cr_2O_3+Nb_2O_3$ lies in the range of 0.01-40 wt %, preferably in the range of 0.1-40 wt %, and the sum formed from $Ag_2O+ZnO+CuO+Cr_2O_3+I—+TeO_2$ and $GeO_2$ lies in the range of 0.140 wt % and the composition is, apart from contaminants, free of Sn.

The fact that the glass is, apart from contaminants, free of Sn, prevents $Ag^+$ from being reduced to $Ag^0$ and thus prevents the occurrence of an undesired discoloration of the glass in the event that Ag is contained in the glass.

In a preferred embodiment, the sum formed from $Na_2O$ and $K_2O$ and $Li_2O$ lies in the range of 0-0.3 wt %.

Antimicrobial activity is understood here to refer to a biocidal or biostatic action against bacteria, fungi, algae, yeast, viruses, etc.

In a further developed embodiment, the Ag content lies in the range of 0.1 wt %<$Ag_2O$≦3 wt %, especially preferred 0.3 wt %<$Ag_2O$≦2 wt %. In order to achieve an especially strong antimicrobial action, the content of $Ag_2O$ is greater than 0.1 wt %, preferably greater than 0.3 wt %, most preferably greater than 1 wt %.

A silver concentration of ≦3 wt % is especially preferred when a strong antimicrobial activity with, at the same time, a reduced discoloration or no discoloration of the glasses is required. Although, owing to the fact that the glass is largely free of Sn, a reduction of $Ag^+$ to $Ag^0$ is prevented for silver concentrations ≦3 wt %, a discoloration can occur even for Sn-free glasses for Ag contents greater than 3 wt %.

A discoloration also for Ag contents greater than 3 wt % can be prevented for Sn-free glasses of the invention by the addition of noble metal oxides, such as $Au_2O_3$, $PtO_2$, $PdO_2$, because these noble metal oxides prevent the reduction of Ag. Preferably, the content of noble metal oxides lies in the range of 0.001 to 100 ppm, preferably in the range of 0.01 to 10 ppm.

Alternatively or in addition, the discoloration due to $Ag_2O$ can be compensated for also for contents greater than 3 wt % by adding one or more ions of rare earths, such as, for example, $Ce^{3+}$, $Pr^{3+}$, $Nd^{3+}$, $Pm^{3+}$, $Eu^{3+}$, $Gd^{3+}$, $Tb^{3+}$, $Dy^{3+}$, $Ho^{3+}$, $Er^+$, $Tm^+$, $Yb^{3+}$, or metals, such as, Ti, V, Cr, Mn, Fe, Co, Ni, Cu, because, for example, complementary color effects are created.

In a preferred embodiment, the ZnO content is >5 wt % ZnO for achieving the antimicrobial action. In particular, in the case when little silver is present in the glass composition, the ZnO content is preferably >10 wt %. Still more preferred is a Zn content of >20 wt %. This is especially preferred in the case when an antimicrobial action of the glass is to be achieved and the glass has a low silver content or, apart from contaminants, is free of silver, in order to prevent a discoloration of the glass.

In a further developed embodiment, the Cu content lies in the range of 0.1 wt %<CuO≦10 wt %, especially preferred 0.5 wt %<CuO≦8 wt %. In order to achieve an adequate microbial action especially against fungi, the content of CuO is greater than 0.1 wt %, preferably greater than 0.5 wt %, still more preferably greater than 1 wt %, most preferably greater than 2 wt %.

In a particularly preferred embodiment of the invention, the glass composition contains both Cu and Ag ions. The combination of Cu and Ag results in a synergistic antimicrobial action. By means of the specific adjustment of the content of Ag and Cu ions in the glass composition, it is possible, in particular, to adjust the bactericidal action and the fungicidal action of the glass.

Cu acts particularly well against fungi; that is, copper has a high fungicidal action. In combination with Ag, the fungicidal action is increased.

In a further developed embodiment, the sum of the Cu content and the silver content lies in the range of 0.1 wt %<CuO+$Ag_2O$≦10 wt %, especially preferred 0.3 wt %<CuO+$Ag_2O$≦8 wt %.

By means of the addition of iodide-ions I—, a wound-healing and disinfecting action is achieved. Iodid ions can be added in the form of AgI, NaI oder KI.

Chromium is used in areas of application in which no toxicological safety is required and a high antimicrobial action is desired.

In a further developed embodiment, the Cr content lies in the range of 0.3 wt %<$Cr_2O_3$≦7 wt %, especially preferred 3 wt %<$Cr_2O_3$≦5 wt %. In order to achieve an adequate antimicrobial action, it is advantageous when the content of $Cr_2O_3$ is greater than 0.3 wt %, preferably greater than 1 wt %, most preferably greater than 2 wt %. A chromium concentration of ≦5 wt % is particularly preferred in the case when a strong antimicrobial activity with, at the same time, a reduced or no discoloration of the glasses is required.

In accordance with the invention, the glass of the glass powder contains $P_2O_5$ as network former, the degree of crosslinking being influenced by, among other things, the melt parameter and it is possible to reduce the fusibility.

When the $P_2O_5$ content is less than 40 wt %, the stability of the glass toward crystallization is too low. When the $P_2O_5$ content is greater than 90 wt %, the corrosion of the crucible material in which the glass composition is fused is too high. Moreover, at high contents of $P_2O_5$, above 80 wt %, the chemical resistance of the glass composition is too low.

Preferably, therefore, the content of $P_2O_5$ lies between 45 and 80 wt %, especially between 60 and 75 wt %.

The glass can contain $B_2O_3$ as an additional network former in order to increase the reactivity. The $B_2O_3$ content preferably does not exceed 60 wt % in order to ensure an adequate chemical resistance. Preferably, the $B_2O_3$ content amounts to 0-50 wt %; in particular, it lies between 1 and 45 wt %.

The glass can contain $SiO_2$ as an additional network former in order to increase the chemical resistance. The $SiO_2$ content should not be higher here than 40 wt %, because, otherwise, the stability toward crystallization is too low and the chemical resistance is too high. Preferably, the $SiO_2$ content lies between 0 and 30 wt %, especially preferred between 1 and 15 wt %.

In an especially preferred embodiment of the invention, the glass composition is largely free of $Al_2O_3$. In an especially preferred embodiment, the content of $Al_2O_3$ is less than 1 wt %.

$Al_2O_3$ is an intermediate oxide, which enhances the connectivity of the glass network. When $Al_2O_3$ is present in too high a concentration, particularly higher than 10 wt %, the chemical resistance of the glasses present is too high. For such Al contents, too low a rate for the liberation of ions, particularly, of Ag and Zn, is observed and the antimicrobial action is very low.

Furthermore, the release of Al is detrimental to health. For example, the liberation thereof can cause diseases such as, for example, Alzheimer's disease. For this reason, it is of particular advantage when the glass is largely free of aluminum. Largely free of aluminum is understood in the present application to mean an $Al_2O_3$ content of less than 1 wt %.

The $Al_2O_3$ content of the composition of the invention amounts, in accordance with the present invention, to at most 10 wt %. Preferably, the $Al_2O_3$ content lies below 5 wt %; especially preferred, the glass is essentially free of aluminum.

The alkaline earth oxides contained in the glass composition of the invention contribute to the construction of the glass network. It is possible to adjust the desired reactivity of the glass by means of the proportion of alkaline earth oxides in the glass composition. Preferred is a range in which the sum formed from MgO+CaO+SrO+BaO lies between 2 wt % and 40 wt %, because a content of MgO+CaO+SrO+BaO of >40 wt % leads to a chemical resistance that is too high and to a reduced reactivity of the glass. When the content of MgO+CaO+SrO+BaO is <2 wt %, the chemical resistance is too low and the water solubility too high. Preferably, therefore, the sum of the alkaline earth oxides lies in the range of 4-35 wt %, preferably in the range of 5-35 wt %.

In an especially preferred embodiment, the sum of the contents of $TiO_2$ and $ZrO_2$ and $BaO$ and $La_2O_3$ and $Nb_2O_3$ lies in the range of 0.1-30 wt %. The addition of such substances makes possible, as described above, the adjustment of the refractive index of the antimicrobial glass composition. In this way, it is possible to adjust the glass material with antimicrobial action, for example, to the refractive index of a polymer, so that the polymer/antimicrobial glass powder mixture is transparent as well. Moreover, cloudiness can be prevented. An especially good adjustability of the refractive index ensues when the antimicrobial glass contains BaO. An especially good adjustability is achieved when the sum of $TiO_2$ and $ZrO_2$ and $BaO$ and $La_2O_3$ and $Nb_2O_3$ is greater than 1 wt %, preferably greater than 5 wt %.

A refractive index adjustment is particularly of advantage when the glass network is used in paints and lacquers. Through the additive of the invention, it is possible to prevent cloudiness. Through the adjustment of the refractive index of the additive to that of the paints and lacquers, the tint of the color is not affected detrimentally by the antimicrobial additive.

By means of the addition of $TiO_2$ and $ZrO_2$ and $BaO$ and $La_2O_3$ and $Nb_2O_3$, it is possible to adjust the refractive index not only in a material volume, but also in a glass surface that has an antimicrobial action.

When the sum of the contents of $TiO_2$ and $ZrO_2$ and $BaO$ and $La_2O_3$ and $Nb_2O_3$ is greater than 40 wt %, particularly greater than 30 wt %, the crystallization resistance of the glass declines strongly and the chemical resistance of the glass becomes very high, so that antimicrobial ions such as silver and copper are liberated only in small quantity and only a very low antimicrobial action is achieved.

A further advantage of the glass composition of the invention is that, by means of the addition of metal ions such as Ti, Ce, Fe, W, Bi, Mo, Nb, UV light is absorbed. Furthermore, through the addition of ions such as Ti, Ce, Fe, W, Bi, Mo, Nb, the yellowing and/or the embrittlement that arises in polymers owing to UV radiation is reduced and even totally prevented.

An especially effective UV blocking is achieved by the addition of only one of the metal ions mentioned above.

The sum of the contents of $TiO_2+CeO_2+Fe_2O_3+WO_3+Bi_2O_3\pm MoO_3+Nb_2O_3$ is less than 20 wt % in the glass compositions of the invention. For contents greater than 20 wt %, the chemical resistance is too high and the reactivity of the glass is too low in order to liberate an adequate quantity of antimicrobial ions. Preferred is the sum $TiO_2+CeO_2+Fe_2O_3+WO_3+Bi_2O_3+MoO_3+Nb_2O_3<15$ wt % and $>0.1$ wt %, preferably $<10$ wt % and $>0.1$ wt %. It is possible to adjust a desired UV absorption by means of the proportion of metal oxides in the glass composition, such as, for example, Ti.

Preferably, the contents of the metal oxides added in addition to Ti lie in the following composition ranges for one or more ions:

| | | |
|---|---|---|
| $CeO_2$ | 0-1 | wt % |
| $Fe_2O_3$ | 0-1 | wt % |
| $WO_3$ | 0-3 | wt % |
| $Bi_2O_3$ | 0-3 | wt % |
| $MoO_3$ | 0-3 | wt % |
| $Nb_2O_3$ | 0-3 | wt % |

In accordance with the invention, another advantage of the largely alkali-free antimicrobial compositions of the invention is that powder made from such glass or glass compositions has an advantage for application in certain polymers comprising synthetic materials or lacquers, because the polymer chain is not ruptured and thus the polymer material is not locally destroyed. In this way, it is ensured that the mechanical and optical properties of the polymer material are not permanently affected in a detrimental manner.

In particular, the polymer chains in polycarbonates, for example, are not attacked, so that the mechanical and optical properties of polycarbonates are not permanently affected in a detrimental manner by the phosphate glass powders according to the invention.

On account of the high phosphorus content, the phosphate glasses, glass powders, glass ceramics or glass ceramic powders, glass flakes, glass beads, and hollow beads of the invention also have, besides their biocidal action due to ion exchange or ion liberation, a bioactive effect. The phosphate glasses, glass ceramics, glass powders, glass ceramic powders, glass flakes, glass beads, and hollow beads, therefore, are especially biocompatible, that is, especially compatible with body tissue.

In a preferred embodiment, the heavy metal content can be reduced by the complete or partial replacement of Zn, for example, preferably by Ca, but also by Mg. Substances of this kind ensure a good environmental compatibility.

For the glasses, glass powders, glass ceramics or glass ceramic powders, glass flakes, glass beads, and hollow beads of the invention, ions are exchanged or liberated by reaction at the glass surface or by partial dissolution of the glass. The antimicrobial action is thus based on, among other things, a liberation of ions, particularly silver ions. The antimicrobial action due to ion exchange or liberation is detrimental to cell growth.

In addition to the release, the antimicrobial glass surface introduced into the system also plays a role. The antimicrobial action of the glass surface is also due to the presence of antimicrobially active ions. It is further known, however, that surface charges, that is, the zeta potential of powders, can have an antimicrobial action particularly on Gram-negative bacteria, because positive surface charges attract bacteria, but Gram-negative bacteria do not grow on surfaces with a positive zeta potential, that is, cannot multiply.

Reference is made in this regard to Bart Gottenbos et al., Materials in Medicine 10 (1999) 853-855, Surface of Polymers.

Antimicrobial actions in powders with positive surface charge are described in Speier et al. Journal of Colloid and Interface Science 89 68-76 (1982), Kenawy et al. Journal of controlled release 50, 145-52 (1998).

Through variation of the glass-forming, that is, the network-forming $P_2O_5$ component, it is possible to adjust the rate of dissolution of the glass. The rate of liberation of biocidal ions is adjusted by the ion exchange and the dissolution of the glass.

In particular, the pH value can be specifically adjusted, particularly to a skin-neutral value, by the liberation of phosphates in aqueous solution.

Through the targeted incorporation of, for example, Ti and/or Zr, furthermore, the network formation is interrupted and the reactivity of the phosphate glass is adjusted, because the biocidally active ions being introduced, such as Zn and Ag, can be more readily released.

For achieving the desired color effects in, for example, applications in paints and lacquers, individual or else several coloring components, such as, for example, $Fe_2O_3$, CoO, CuO, $V_2O_5$, $Cr_2O_5$, can be added to the glasses in a total concentration that is less than 4 wt %, preferably less than 1 wt %.

The biocidal or biostatic action of the glass of the invention or the glass powders obtained therefrom or of the glass ceramics of the invention or glass ceramic powders obtained from these starting glasses is caused by ion liberation in a liquid medium, particularly in water. The glasses or the glass powders and glass ceramics obtained therefrom have a biocidal action against bacteria and fungi as well as viruses, algae, and yeast.

The addition of silver, as described above, very often leads to discolorations of the glass. Such discoloration can be prevented when silver in mixture is added to the glass in oxidatively active form—for example, as silver nitrate ($AgNO_3$). Furthermore, the glass is fused under oxidizing conditions—for example, by means of oxygen bubbling—in order to achieve an oxidative state in the glass and thus to prevent a reduction of the $Ag^+$ to metallic $Ag^0$. This can be achieved also by adjustments of the furnace tank, such as, for example, by oxidative burner adjustments. When the process is conducted in such a manner and silver is added, it is possible to prevent a discoloration both in the glass and also during the subsequent processing in the polymer. Other components, such as, for example, alkalis or alkaline earths can also be preferably added as oxidatively active components, such as, for example, nitrates, peroxides, etc., which are added to the mixture.

In comparison to the silicate glasses known from the prior art, the phosphate glasses described here have a higher reactivity and thus a better antimicrobial activity. Furthermore, the phosphate glasses described here have a lower glass temperature (Tg) and can thus be processed at lower temperatures and thus processed more easily. Furthermore, when the glasses described here, which melt at relatively low temperatures, are mixed with high-melting polymers, there can ensue a partial or complete fusion of the glasses so that the glasses form a more intimate connection to the polymer, which can lead all the way to an extremely homogeneous distribution in the polymer. A fusion of the glasses, as described, can be achieved during, for example, the processing of polymer-glass composite materials of the invention to semifinished plastic goods or plastic products with biocidal properties. In this regard, reference is made, in particular, to the fusion during extrusion of the polymer-glass composite materials. Through this fusion, the antimicrobial activity is increased and a higher strength of the polymer-glass composite material is achieved. Furthermore, the combustibility or temperature resistance of the material is increased. For the silicate glasses that are known from the prior art—for example, the silicate glasses known from PCT/EP03/00559—which can be admixed to synthetic materials, such a fusion is not observed. Moreover, the antimicrobial action of such mixtures is markedly lower than for mixtures of synthetic materials with the glasses according to the invention. Furthermore, the refractive index can be specifically adjusted by adding, for example, Ti and/or Zr.

By means of grinding processes, glass compositions can be ground to glass powders with particle sizes of <100 μm. Particle sizes of <50 μm or 20 μm have proven appropriate. Especially suitable are particle sizes of <10 μm as well as smaller than 5 μm. Particle sizes of <2 μm or <1 μm have been found to be most especially suitable.

The glass composition or the glass ceramics obtained therefrom or the glass powders or glass ceramic powders, glass fibers, glass granulates, or glass beads obtained therefrom can be employed in the field of cosmetics/medicine, because, as a rule, they are toxicologically safe.

The embodiments of the invention, which are characterized as toxicologically unobjectionable, are suitable especially for a use in creams or lotions or similar forms of administration in order to apply them to the skin.

In the field of medicine, the reduction or prevention of skin irritations, such as reddening of the skin and irritation, as well as the treatment of wounds in the cosmetic and medical fields are possible applications.

Another field of application is the preservation of foods.

For applications in fields in which the glass, the glass ceramics obtained therefrom, or the glass powders or glass ceramic powders come into contact with humans—for example, for applications in the fields of medicine, cosmetics, etc, the glass is preferably free of other heavy metals. For such applications, it is preferred that especially pure raw materials are used as well.

The glasses, glass powders, glass ceramics or glass ceramic powders, glass fibers, glass granulates, and glass beads of the invention can also be used for preserving the products themselves as well as for achieving an antimicrobial action toward the outside, that is, a release of antimicrobially active substances, particularly ions, such as, for example, zinc or silver.

For the use of the glass compositions or glass ceramics or glass powders or glass ceramic powders, glass fibers, glass granulates, glass beads for achieving an antimicrobial/biocidal action in products—for example, in paints and lacquers—the toxicological safety is not a condition. For such uses, the composition can contain $Cr_2O_3$ and/or CuO.

The glass compositions or glass ceramics or glass powder or glass ceramic powder, glass fibers, glass granulates, glass beads of the invention can be used in this field for preserving the products themselves and/or for achieving an antimicrobial action toward the outside, that is, a release of antimicrobially active substances, particularly of ions, such as, for example, zinc or silver.

The glass or the glass ceramic or the glass powder or glass ceramic powder, glass fibers, glass granulates, glass beads can be applied, when their hydrolytic resistance is adequate, as a coating, that is, a protective layer, on a polymer.

The biocidal or biostatic action of the glass of the invention or the glass powder obtained therefrom or of the glass ceramics of the invention obtained from these starting glasses is caused by ion liberation in a liquid medium, particularly in water. The glasses or the glass powders and glass ceramics obtained therefrom have biocidal action toward bacteria, fungi, and algae as well as viruses. This action can be caused particularly by the presence of silver and zinc.

A preferred field of application of the glasses or the glass ceramics, glass powders, or glass ceramic powders obtained therefrom according to the invention is the use in polymers for achieving a biocidal or biostatic action. On the one hand, a preservation of the polymer itself can be of primary concern, that is, the protection of the polymer against bacteria and against fungal attack. On the other hand, a biostatic or biocidal polymer surface can be created in this way, in which, insofar as possible, no biocidally active substances—for example, ions—are released into the environment. A further goal can be to provide a polymer that liberates the active substance, which, in particular, is biocidal.

Provided in a further aspect of the invention, therefore, is a plastic-glass composite material, this plastic-glass composite material comprising:

a plastic material a glass and/or a glass ceramic based on a glass composition comprising in wt %

| | |
|---|---|
| $P_2O_5$ | >45-90 wt % |
| $B_2O_3$ | 0-60 wt % |
| $SiO_2$ | 0-40 wt % |
| $Al_2O_3$ | 0-20 wt % |
| $SO_3$ | 0-30 wt % |
| $Li_2O$ | 0-0.1 wt % |
| $Na_2O$ | 0-0.1 wt % |
| $K_2O$ | 0-0.1 wt % |
| CaO | 0-40 wt % |
| MgO | 0-40 wt % |
| SrO | 0-15 wt % |
| BaO | 0-40 wt % |
| ZnO | 0-40 wt % |
| $Ag_2O$ | 0-5 wt % |
| CuO | 0-15 wt % |
| $Cr_2O_3$ | 0-10 wt % |
| I | 0-10 wt % |
| $TeO_2$ | 0-10 wt % |
| $GeO_2$ | 0-10 wt % |
| $TiO_2$ | 0-10 wt % |
| $ZrO_2$ | 0-10 wt % |
| $La_2O_3$ | 0-10 wt % |
| $Nb_2O_3$ | 0-5 wt % |
| $CeO_2$ | 0-5 wt % |
| $Fe_2O_3$ | 0-5 wt % |
| $WO_3$ | 0-5 wt % |
| $Bi_2O_3$ | 0-5 wt % |
| $MoO_3$ | 0-5 wt % | in which the sum formed from $Ag_2O+ZnO+CuO+Cr_2O_3+I+TeO_2$ and $GeO_2$ lies in the range of 0.1-40 wt % and the sum formed from $TiO_2+ZrO_2+BaO+La_2O_3+Cr_2O_3+Nb_2O_3$ lies in the range of 0.01-40 wt % and the composition is, apart from contaminants, free of Sn.

For glass compositions in polymers, it is expected that, owing to the screening by aqueous media, they are only inadequately antimicrobial, because they are encapsulated by the polymers. Surprisingly, it was found that, even through the addition of very small quantities of biocidally active ions, such as Ag, Zn, Cu, a significant antimicrobial action of the glass, the glass ceramics, the glass powder, or the glass ceramic powder arises.

This is surprising for the reason that the very small water content is adequate in conventionally produced polymers to "activate" biocidal ions in the glass matrix and thus to achieve a long-term antimicrobial action. If the polymer-glass composite, which contains such glass compositions, glass ceramics, glass powders, or glass ceramic powders, is heated, the glass, depending on the adjusted processing temperature, can partially melt and this results in an increase in the antimicrobial action. Other properties of the composite material, such as, for example, the strength, are also positively influenced.

As discussed above, the glasses with the compositions of the invention or the glass ceramics, glass powders, or glass ceramic powders obtained therefrom have a biostatic or biocidal action in polymers. This can be exploited to preserve the polymers, particularly to prevent fungal attack or decomposition by bacteria. Also conceivable is the provision of a polymer with an antimicrobial surface. In the case of such an antimicrobial surface, there should occur, insofar as possible, no liberation or release of antimicrobially active substances, particularly ions, toward the outside, that is, outside of the polymer surface.

The glasses of the invention also make possible a slow release of antimicrobially active ions from a polymer matrix. Here, the water content of the polymer as well as the diffusion of the mobile ions in the polymer matrix plays the decisive role. Here, in general, the contents of biocidal ions in the glass matrix are also higher or the concentration of the glass in the polymer is higher than in the application referred to above.

This liberation can be associated with a partial or complete dissolution of the glass. In an especially preferred embodiment, the polymer matrix also dissolves partially or completely. This is the case, in particular, when the polymer matrix is water-soluble.

Surprisingly, it has been found that a strong antimicrobial action is achieved even without the presence of alkalis in the glass matrix. Usually, the reactivity of the glass and thus the strength of the antimicrobial action both in terms of time and in quantitative terms is adjusted via the content of alkali ions. In the glasses described here, it is possible to adjust a differing reactivity even with a smaller content for largely alkali-free glass compositions. For glasses of the invention, alkaline earths of the glass are exchanged for $H^+$ ions of the aqueous medium through reactions at the surface of the glass.

In one embodiment of the invention, the glass additive is contained in the polymer itself. In an alternative embodiment of the invention, the glass additive can be applied to the polymer also with a precursor material, for example, as a coating or protective layer.

Glass ceramics or ceramics can be obtained from the glasses described here. These are produced by way of a subsequent heat-up step either on the semifinished product (for example, the glass strips or ribbons) or on the product—for example, on the glass powders or the glass fibers. Subsequent to the annealing step, a regrinding may be necessary in order to adjust the desired particle size.

Depending on the particle size, the concentration, and the composition of the powder, pH values with a lower limit of <1.0, preferably <1.5, most especially preferred <2 are obtained. The upper limit amounts to <9.0 and 8.0, preferably 7.5 and 7.0, and most especially preferred <6.

The grinding process can be carried out both dry and with nonaqueous or aqueous grinding media.

Mixtures of different glass powders from the composition range with different compositions and particle sizes are possible in order to combine certain effects.

Mixtures of powders with different particle sizes can be used in order to combine a strong but short-term antimicrobial action with a long-term antimicrobial action.

A preferred embodiment comprises a mixture of two or more powders, wherein one powder, in accordance with the composition range described, has a particle size distribution d50 of 8-500 µm, preferably 10-100 µm, most especially preferred 10-30 µm, another powder has a particle size distribution d50 of 0.01-100 µm, preferably 0.1-20 µm, most especially preferred 0.5-2 µm Another preferred embodiment comprises a mixture of two or more powders, wherein the ratios of the specific surface areas of the one powder to the other powder of the mixture are 0.001 to 100, preferably 0.01 to 50, especially preferred 0.1 to 10.

Mixtures of glass powders with different compositions and particle sizes can be combined for adjusting special properties of the individual glass powders synergistically. Thus, it is possible, for example, to control the antimicrobial action of the glass powder by means of the particle size.

Besides the direct introduction into the glass matrix during the melt process, these ions can also be introduced via an ion exchange only into the surface regions of the glass.

The glass of the invention does not give rise to any skin-irritating effects in an especially preferred embodiment.

By means of a combination of the pH effect, the action through surface effects, and the Ag, Cu, or Zn release, it is possible to achieve a substantial increase in the antimicrobial action which goes markedly beyond the sum of the individual effects. The concentrations of Ag, Cu, Zn ions released into the product can lie here markedly below 1 ppm.

The introduction of Ag, Cu, Zn can occur here either already during the melting by means of corresponding salts or else through ion exchange of the glass after the melting.

Glasses, glass powders, glass ceramics, or glass ceramic powders with a composition that lies within the claimed composition range fulfill all requirements in regard to a use in the fields of hygienic paper products, cosmetics, paints, lacquers, polymers, plasters, medical products, cosmetic applications, food additives as well as use in deodorant products and antiperspirants as well as in products for treating skin irritations and acute and chronic wounds as well as in the field of dental care/dental hygiene and oral care/oral hygiene as well as for dental materials in, for example, tooth fillings, crowns, inlays, etc.

The glass, the glass ceramics, the glass-glass ceramic powder can be employed in any suitable form. Mixtures of different glass powders from the composition range with different compositions are also possible. The mixture with other glass powders is also possible in order to combine certain effects.

Components such as fluorine can be added, depending on the area of application, to the glass up to concentrations of a total of 5 wt %. This embodiment finds application especially in the area of dental care and dental hygiene, because, besides the antimicrobial and anti-inflammation action due to this embodiment, fluorine, which hardens the dental enamel can be released in low concentration.

An especially preferred application is the use of the described glasses for dental materials, particularly for tooth fillings, crowns, inlays. Especially preferred here is the use as a composite material with polymer materials.

Without limiting the use of the described alkali-free glasses in the polymer field, there are polymers that are especially suitable for the addition of the glasses described here. These are, in particular, PMMA, PVC, PFTE, polystyrene, polyacrylate, polyethylene, polyester, polycarbonate, PGA biodegradable polymer, LGA biodegradable polymer or the biopolymers collagen, fibrin, chitin, chitosan, polyamides, polycarbonates, polyesters, polyimides, polyurea, polyurethanes, organic fluoropolymers, polyacrylamides and polyacrylic acids, polyacrylates, polymethacrylates, polyolefins, polystyrenes and styrene copolymers, polyvinyl esters, polyvinyl ethers, polyvinylidene chloride; vinyl polymers, polyoxymethylene, polyaziridines, polyoxyalkylenes, synthetic resins or alkyl resins, amino resins, epoxy resins, phenolic resins, or unsaturated polyester resins, electrically conductive polymers, high-temperature polymers, inorganic polymers, polyphenyl oxide silicones, biopolymers containing, for example, cellulose, cellulose esters, cellulose ethers, enzymes, gelatins, natural resins, nucleic acids, polysaccharides, proteins, silk, starch, or wool.

Especially preferred is the use of the glasses described here for polymers that are known to show an alkali incompatibility, such as, for example, polycarbonates, for which alkali ions can lead to chain rupture.

In particular, they are suitable for use in the following products as, for example, an antimicrobial additive in polymers:

cutting boards gloves waste containers knife handles cutlery—for example, chopsticks trays tablecloths refrigerators dishwashers washer-dryers washing machines telephones keyboards flat irons rice cookers steering wheels automobile panels armrests keys door handles ash trays manual shifts switches ballpoint pens diskettes audio-video cassettes compact disks (CDs)

clipboards

Furthermore, such glasses, glass ceramics, glass powders or even glass ceramic powders can also find use in the area of the clothing industry, preferably as an additive to synthetic fibers. A use in articles of clothing socks underwear hand cloths sanitary napkins wallpaper pillow covers pillow fillings swimming apparel bathing caps is conceivable.

Additional products based on synthetic fibers or polymers that contain the glass of the invention, the glass ceramics of the invention, or a glass or glass ceramic powder obtained therefrom can be:

carpets contact lenses contact lens holders—containers play sand plastic money paper money toys wristwatches diving suits The antimicrobial glass powder is especially suitable for use in fibers for carpets as an admixture to the fibers.

The glass described in this invention or the glass ceramics obtained therefrom or the glass or glass ceramic powder obtained therefrom, which is obtained by grinding, is water-soluble, but has an adequate chemical resistance. The glass or the glass powder acts, first and foremost, by means of ion exchange or ion release, which is associated with a surface reaction, and a liberation of metal ions.

Surprisingly, the glass or glass ceramic powder of the invention shows a high reactivity and a higher antimicrobial action than the bioactive, alkali-free glasses that have been described in the prior art, or glass powders that are prepared from such glasses.

The invention will be described below on the basis of embodiment examples as well as the figures.

BRIEF DESCRIPTION OF THE SEVERAL VIEWS OF THE DRAWINGS

FIG. 1: Transmission spectrum for various glass powders.

DETAILED DESCRIPTION OF THE INVENTION

The glasses described can also be produced via sol-gel processes in addition to the conventional melt process.

The glass was fused out of raw materials in a silica glass crucible and subsequently processed into ribbons. The ribbons were further processed by means of dry grinding to produce powders with a particle size of d50=4 μm. Platinum crucibles, quartz crucibles, or ZAC crucibles (ZAC: baddelyte-corundum-stone) can also serve as the melt crucibles. Involved in the case of ZAC is melt-cast zirconium aluminum oxide. Quartz crucibles are made, as a rule, out of sintered quartz glass powder or coarse quartz glass sand, the sintered quartz glass powder or coarse quartz glass sand being porous.

Presented in Table 1 are the compositions and properties of alkali-free glasses that can be ground to produce the glass powders of the invention. The compositions refer to the synthesis values in wt % based on oxide.

TABLE 1

Compositions (synthesis values) [wt %] of glass compositions of the invention

| | Wt % | | | | | | | | | | | | |
|---|---|---|---|---|---|---|---|---|---|---|---|---|---|
| | Emb. Ex. 1 | Emb. Ex. 2 | Emb. Ex. 3 | Emb. Ex. 4 | Emb. Ex. 5 | Emb. Ex. 6 | Emb. Ex. 7 | Emb. Ex. 8 | Emb. Ex. 9 | Emb. Ex. 10 | Emb. Ex. 11 | Emb. Ex. 12 | Emb. Ex. 13 |
| $P_2O_5$ | 70 | 62 | 71 | 66 | 70 | 66 | 66.5 | 63 | 66 | 69 | 71 | 70 | 55 |
| $B_2O_3$ | 10 | 20 | 0 | 10 | 4 | 8 | 7 | 12.5 | 7 | 0 | 1 | 10 | 15 |
| $SiO_2$ | 1 | 8 | 4 | 1 | | 3 | | 1 | 0.5 | 4 | 2 | 1 | |
| $Al_2O_3$ | | 0.5 | 6 | 0 | | | | | 0.5 | 0 | 6 | | 1 |
| $SO_3$ | | | 6 | | | | | | | | | | |
| CaO | 3.5 | | 3 | | 8 | 9 | 10 | 9 | 10 | 3 | 7 | 3 | |
| MgO | | | | | | 12 | | 13 | 13.5 | 15 | | | |
| BaO | 12 | 5 | | 15 | | | | | | | 2 | | 5 |
| ZnO | | | | | 15 | | 13 | | | | 14 | 11 | |
| $TiO_2$ | 1 | | 1 | | 3 | | | 1 | 1 | | | 3 | 2 |
| $ZrO_2$ | 1 | 1.5 | 1 | | | 0.5 | 1 | | | | 1 | | 2 |
| $Ag_2O$ | 1.5 | 3 | 3 | 1 | | 1 | 0.5 | 1.5 | 2 | 2 | 2 | 2 | 2 |
| CuO | 2 | | 8 | 5 | | | | | | | | | |
| $Cr_2O_3$ | | | | | | | | | | | | | |
| $Nb_2O_3$ | | | 2 | | | | | | | | | | |
| $La_2O_3$ | | | | 2 | | | | | | | | | |
| $Bi_2O_3$ | | | | | | | | | | | | | |
| $WO_3$ | | | | | | | | | | | | | |
| $MoO_3$ | | | | | | | | | | | | | |
| $CeO_2$ | | | | | | | | | | | | | |
| $Fe_2O_3$ | | | | | | 1.5 | | | | | | | |
| $Au_2O_3$ | | 10 | 1 | | | | | | | | | | |
| $PdO_2$ | | ppm | | | | | | | | | | | |
| $Dy_2O_3$ | | | | | | | | | | | | | |

| | Wt % | | | | | | | |
|---|---|---|---|---|---|---|---|---|
| | Emb. Ex. 14 | Emb. Ex. 15 | Emb. Ex. 16 | Emb. Ex. 17 | Emb. Ex. 18 | Emb. Ex. 19 | Emb. Ex. 20 | Emb. Ex. 21 |
| $P_2O_5$ | 72 | 68 | 66 | 68 | 68 | 66.6 | 66.3 | 66.3 |
| $B_2O_3$ | 1 | 8 | 10 | 8 | 8 | 7.22 | 7.2 | 7.2 |
| $SiO_2$ | 1 | 1 | 1 | 1 | 0.5 | 0.2 | 0.7 | 0.2 |
| $Al_2O_3$ | | | | | | | 0.4 | 0.4 |
| $SO_3$ | | | | | | | | |
| CaO | 6 | 6 | | | | 8.73 | 9.7 | 9.7 |
| MgO | 6 | | | | | | | |
| BaO | | | 18 | 16 | 16 | 13.74 | 13.7 | 13.7 |
| ZnO | 9 | 12 | | | | | | |
| $TiO_2$ | | | 1 | 1 | 1.5 | 1 | | 0.5 |

TABLE 1-continued

Compositions (synthesis values) [wt %] of glass compositions of the invention

| | | | | | | | | |
|---|---|---|---|---|---|---|---|---|
| $ZrO_2$ | 3 | | 2 | 2 | 2 | 0.5 | | |
| $Ag_2O$ | 2 | 2 | 2 | 2 | 2 | 2 | 2 | 2 |
| $CuO$ | | | | | | | | |
| $Cr_2O_3$ | | | | | | | | |
| $Nb_2O_3$ | | | | | | | | |
| $La_2O_3$ | | | | | | | | |
| $Bi_2O_3$ | | | | | | | | |
| $WO_3$ | | | | | | | | |
| $MdO_3$ | | | | | | | | |
| $CeO_2$ | | | | | | | | |
| $Fe_2O_3$ | | | | | | | | |
| $Au_2O_3$ | | | | | | | | |
| $PdO_2$ | | | | | | | | |
| $Dy_2O_3$ | | | | | | | | |

To be presented below for some of the embodiment examples referred to above are the pH values, the conductivities, the refractive index, the transmission behavior, the rate of Ag ion liberation, and the chemical resistance.

Presented in Table 2 are the pH values and the conductivity of 1 wt % glass powders of the glass compositions according to Embodiment Examples 11-15 in Table 1 in aqueous solution:

TABLE 2 pH value and conductivity value, 1 wt % power in aqueous solution

| | After 15 min | | After 60 min | | After 24 hours | |
|---|---|---|---|---|---|---|
| | pH value | Conductivity [µS/cm] | pH value | Conductivity [µS/cm] | pH value | Conductivity [µS/cm] |
| Emb. Ex. 11 | 2.65 | 726 | 2.52 | 1011 | 2.03 | 2740 |
| Emb. Ex. 12 | 2.70 | 998 | 2.24 | 1290 | 1.97 | 2700 |
| Emb. Ex. 13 | 2.71 | 639 | 2.45 | 872 | 2.19 | 2170 |
| Emb. Ex. 14 | 2.64 | 692 | 2.40 | 1049 | 2.10 | 2880 |
| Emb. Ex. 15 | 2.39 | 1285 | 2.14 | 1726 | 1.78 | 4530 |

Presented in Table 3, as a measure of the chemical resistance, is the weight loss of 1 wt % glass powder of a glass composition according to one of the Embodiment Examples 12 to 16 in aqueous solution at room temperature (RT) as a function of time:

TABLE 3

Chemical resistance (weight loss of 1 wt % glass powder in aqueous solution at room temperature (RT))

| | Weight loss [%] | |
|---|---|---|
| | 1 h, RT | 24 h, RT |
| Emb. Ex. 12 | 7.3 | 27.9 |
| Emb. Ex. 13 | 8.3 | 22.4 |
| Emb. Ex. 14 | 7.1 | 22.6 |
| Emb. Ex. 15 | 15.9 | 49.4 |
| Emb. Ex. 16 | 11.6 | 37.3 |

Presented in Table 4 is the silver ion liberation (of 1 wt % glass powder) of a glass composition according to one of the Embodiment Examples 12 to 16.

TABLE 4

| | Silver ion liberation | |
|---|---|---|
| | 1 hour | 24 hours |
| Emb. Ex. 12 | 17.4 mg/L | 54.7 mg/L |
| Emb. Ex. 13 | 16.1 mg/L | 43.7 mg/L |
| Emb. Ex. 14 | 14.8 mg/L | 46.0 mg/L |
| Emb. Ex. 15 | 30.5 mg/L | 94.9 mg/L |
| Emb. Ex. 16 | 23.1 mg/L | 73.1 mg/L |

Presented in Table 5 is the antibacterial action of a glass powder according to the Europ. Pharmacopoeia (3rd edition) for a glass composition according to Embodiment Example 9 in Table 1 with a particle size of 4 µm in an aqueous suspension at a concentration of 0.01 wt %. The glass was not heated up before grinding. Here, the respective starting value refers to the bacteria count at the beginning of the test and the following value refers to the bacteria count after the specified time. Here, a value of 0 refers to the fact that no bacteria are present any longer, this substantiating the antimicrobial action of the glass powder.

TABLE 5

Antibacterial action of a glass powder in aqueous solution according to Embodiment Example 9

|  | E. coli | P. aeruginosa | S. aureus | C. albicans | A. niger |
|---|---|---|---|---|---|
| Start | 350,000 | 250,000 | 270,000 | 330,000 | 240,000 |
| 2 days | 0 | 0 | 0 | 0 | 100 |
| 7 days | 0 | 0 | 0 | 0 | 100 |
| 14 days | 0 | 0 | 0 | 0 | 0 |
| 21 days | 0 | 0 | 0 | 0 | 0 |
| 28 days | 0 | 0 | 0 | 0 | 0 |

Presented in Table 6 are the refractive indices nD for the glass powder according to Embodiment Example 9 to Embodiment Example 21 in Table 1. As can be seen from Table 6, the refractive index can be adjusted by adding, for example, $TiO_2$ and/or $ZrO_2$ and/or BaO and/or $La_2O_3$, and/or $Cr_2O_3$, and/or $Nb_2O_3$.

TABLE 6

| | Refractive index | | | | | | | | | | | |
|---|---|---|---|---|---|---|---|---|---|---|---|---|
| | Emb. Ex. 9 | Emb. Ex. 10 | Emb. Ex. 11 | Emb. Ex. 12 | Emb. Ex. 13 | Emb. Ex. 15 | Emb. Ex. 16 | Emb. Ex. 17 | Emb. Ex. 18 | Emb. Ex. 19 | Emb. Ex. 20 | Emb. Ex.21 |
| nD | 1.55 | 1.51 | 1.53 | 1.55 | 1.55 | 1.54 | 1.56 | 1.56 | 1.57 | 1.58 | 1.57 | 1.58 |

As seen from the above table, the refractive indices nD of the glass powders that were obtained from the glass compositions in Table 1 lie between 1.51 and 1.59 and thus in the range of the refractive indices of polymers. For example, the refractive index of polystyrene is nD polystyrene=1.59, that of polycarbonate is nD polycarbonate=1.58, that of polyester is nD polyester=1.57, that of polyamide is nD polyamide=1.53.

By means of the glass compositions of the invention, it is thus possible to make available an antimicrobial glass powder whose refractive index is adjusted to that of the polymer, so that a cloudiness is largely prevented and a high transparency z is afforded, because, for example, scattering effects of particles with different refractive indices are prevented.

As the transmission spectra in FIG. 1 show for different glass compositions in Table 1, it is possible, through the targeted use of UV-blocking ions, such as, for example, Ti, to change the UV edge.

By means of this UV blocking, the yellowing and/or the embrittlement due to UV radiation can be reduced in polymers or even totally eliminated.

In FIG. 1, the transmission spectrum for Embodiment Example 8 is indicated by reference 100, for Embodiment Example 9 by 102, for Embodiment Example 10 by 104, for Embodiment Example 11 by 106, for Embodiment Example 12 by 108, for Embodiment Example 13 by 110, and for Embodiment Example 15 by 112. The transmission is measured on solid samples, the thickness of the samples amounting to 8 mm.

As seen from the following Table 7, a sample with 0.5 wt % glass powder according to Embodiment Example 10 (Table 1) in polystyrene satisfies the ASTM E 2180-1 test for an antimicrobial action. The tested germ strain is *Escherichia coli*.

TABLE 7

| | ASTM E 2180-1 | |
|---|---|---|
| | Germ count on the polymer sample after 0 hours.: Start value | Germ count on the polymer sample after 24 hours |
| 0.5 wt % Glass powder according to Emb. 10 in polystyrene | 1.5 E+06 | 1.0 E02 |

Emb. 10: Reduction by 4 logarithmic steps: strong bacterial/fungicidal action (after 24 hours)

Analysis after 24 hours:

<1 log step (power of ten): no significant bactericidal//fungicidal action

>1 power of ten <2 powers of ten: low bactericidal/fungicidal action

>2 powers of ten <3 powers of ten: significant bactericidal/fungicidal action

>3 log step (power of ten): strong bacterial/fungicidal action

The invention claimed is:

1. An antimicrobially acting phosphate glass composition comprising, in weight percent on an oxide basis:
   between greater than 45 and less than or equal to 90 of $P_2O_5$;
   0 to 55 of $B_2O_3$;
   0 to 40 of $SiO_2$;
   0 to 20 of $Al_2O_3$;
   0 to 30 of $SO_3$;
   0 to 0.1 of $Li_2O$;
   0 to 0.1 of $Na_2O$;
   0 to 0.1 of $K_2O$;
   0 to 40 of CaO;
   0 to 40 of MgO;
   0 to 15 of SrO;
   0 to 40 of BaO;
   0 to 40 of ZnO;
   greater than 0.1 but less than or equal to 3 of $Ag_2O$;
   0 to 15 of CuO;
   0 to 10 of $Cr_2O_3$;
   0 to 10 of I;
   0 to 10 of $TeO_2$;
   0 to 10 of $GeO_2$;
   0 to 10 of $TiO_2$;
   0 to 10 of $ZrO_2$;
   0 to 10 of $La_2O_3$;
   0 to 5 of $Nb_2O_3$;
   0 to 5 of $CeO_2$;
   0 to 5 of $Fe_2O_3$;
   0 to 5 of $WO_3$;

0 to 5 of $Bi_2O_3$; and
0 to 5 of $MoO_3$,
wherein a first sum formed from the $TiO_2$, the $ZrO_2$, the $BaO$, the $La_2O_3$, the $Cr_2O_3$, and the $Nb_2O_3$ lies in a range of 0.01 to 40 weight percent on oxide basis, wherein a second sum formed from the $Ag_2O$, the $ZnO$, the $CuO$, the $Cr_2O_3$, the $I$, the $TeO_2$, and the $GeO_2$ lies in a range of 0.1 to 40 weight percent on oxide basis, and wherein the composition is free of non-contaminant Sn.

2. The antimicrobially acting phosphate glass composition according to claim 1, wherein the second sum lies in a range of 0.5 to 40 weight percent on oxide basis.

3. The antimicrobially acting phosphate glass composition according to claim 1, wherein the second sum lies in a range of 2.0 to 40 weight percent on oxide basis.

4. The antimicrobially acting phosphate glass composition according to claim 1, wherein the ZnO is present in greater than 5 weight percent on oxide basis.

5. The antimicrobially acting phosphate glass composition according to claim 1, wherein the CuO lies in a range greater than 0.1 weight percent on oxide basis but less than or equal to 10 weight percent on oxide basis.

6. The antimicrobially acting phosphate glass composition according to claim 1, further comprising a third sum of the CuO and the $Ag_2O$ lying in a range of greater than 0.1 weight percent on oxide basis and less than or equal to 10 weight percent on oxide basis.

7. The antimicrobially acting phosphate glass composition according to claim 1, wherein the $Cr_2O_3$ lies in a range of greater than 0.3 weight percent on oxide basis but less than or equal to 7 weight percent on oxide basis.

8. The antimicrobially acting phosphate glass composition according to claim 1, wherein the $Al_2O_3$ is present in less than 1 weight percent on oxide basis.

9. The antimicrobially acting phosphate glass composition according to claim 1, further comprising a sum formed from the MgO, GaO, SrO, and BaO lies in a range of 2-40 weight percent on oxide basis.

10. The antimicrobially acting phosphate glass composition according to claim 1, further comprising a fifth sum of the $TiO_2$, $CeO_2$, $Fe_2O_3$, $WO_3$, $Bi_2O_3$, $MoO_3$, and $Nb_2O_3$ that is present in less than 20 weight percent on oxide basis.

11. The antimicrobially acting phosphate glass composition according to claim 1, wherein the antimicrobially acting phosphate glass is usable in glass ceramics.

12. The antimicrobially acting phosphate glass composition according to claim 1, wherein the antimicrobially acting phosphate glass is usable in a glass powder or a glass ceramic powder.

13. The antimicrobially acting phosphate glass composition according to claim 12, wherein the glass powder or ceramic glass powder has particles having a size, on average, less than 20 μm.

14. The antimicrobially acting phosphate glass composition according to claim 12, wherein the glass powder or ceramic glass powder has particles having a size of, on average, less than 5 μm.

15. The antimicrobially acting phosphate glass composition according to claim 12, wherein the glass powder or ceramic glass powder has particles having a size, on average, less than 1 μm.

16. An antimicrobially acting phosphate glass composition comprising, in weight percent on an oxide basis:
between greater than 45 and less than or equal to 90 of $P_2O_5$;
0 to 55 of $B_2O_3$;
0 to 40 of $SiO_2$;
0 to 20 of $Al_2O_3$;
0 to 30 of $SO_3$;
0 to 0.1 of $Li_2O$;
0 to 0.1 of $Na_2O$;
0 to 0.1 of $K_2O$;
0 to 40 of CaO;
0 to 40 of MgO;
0 to 15 of SrO;
0 to 40 of BaO;
greater than 5 to 40 of ZnO;
0 to 5 of $Ag_2O$;
0 to 15 of CuO;
0 to 10 of $Cr_2O_3$;
0 to 10 of I;
0 to 10 of $TeO_2$;
0 to 10 of $GeO_2$;
0 to 10 of $TiO_2$;
0 to 10 of $ZrO_2$;
0 to 10 of $La_2O_3$;
0 to 5 of $Nb_2O_3$;
0 to 5 of $CeO_2$;
0 to 5 of $Fe_2O_3$;
0 to 5 of $WO_3$;
0 to 5 of $Bi_2O_3$; and
0 to 5 of $MoO_3$,
wherein a first sum formed from the $TiO_2$, the $ZrO_2$, the $BaO$, the $La_2O_3$, the $Cr_2O_3$, and the $Nb_2O_3$ lies in a range of 0.01 to 40 weight percent on oxide basis, wherein a second sum formed from the $Ag_2O$, the $ZnO$, the $CuO$, the $Cr_2O_3$, the $I$, the $TeO_2$, and the $GeO_2$ lies in a range of <5 to 40 weight percent on oxide basis, and wherein the composition is free of non-contaminant Sn.

17. The antimicrobially acting phosphate glass composition according to claim 16, wherein the antimicrobially acting phosphate glass is usable in glass ceramics.

18. The antimicrobially acting phosphate glass composition according to claim 16, wherein the antimicrobially acting phosphate glass is usable in a glass powder or a glass ceramic powder.

19. The antimicrobially acting phosphate glass composition according to claim 18, wherein the glass powder or ceramic glass powder has particles having a size, on average, less than 20 μm.

20. An antimicrobially acting phosphate glass composition comprising, in weight percent on an oxide basis:
between greater than 45 and less than or equal to 90 of $P_2O_5$;
0 to 55 of $B_2O_3$;
0 to 40 of $SiO_2$;
0 to 20 of $Al_2O_3$;
0 to 30 of $SO_3$;
0 to 0.1 of $Li_2O$;
0 to 0.1 of $Na_2O$;
0 to 0.1 of $K_2O$;
0 to 40 of CaO;
0 to 40 of MgO;
0 to 15 of SrO;
0 to 40 of BaO;
0 to 40 of ZnO;
0 to 5 of $Ag_2O$;
0 to 15 of CuO;
greater than 0.3 but less than or equal to 7 of $Cr_2O_3$;
0 to 10 of I;
0 to 10 of $TeO_2$;
0 to 10 of $GeO_2$;
0 to 10 of $TiO_2$;
0 to 10 of $ZrO_2$;

0 to 10 of $La_2O_3$;
0 to 5 of $Nb_2O_3$;
0 to 5 of $CeO_2$;
0 to 5 of $Fe_2O_3$;
0 to 5 of $WO_3$;
0 to 5 of $Bi_2O_3$; and
0 to 5 of $MoO_3$,
wherein a first sum formed from the $TiO_2$, the $ZrO_2$, the $BaO$, the $La_2O_3$, the $Cr_2O_3$, and the $Nb_2O_3$ lies in a range of >0.3 to 40 weight percent on oxide basis, wherein a second sum formed from the $Ag_2O$, the $ZnO$, the $CuO$, the $Cr_2O_3$, the I, the $TeO_2$, and the $GeO_2$ lies in a range of >0.3 to 40 weight percent on oxide basis, and wherein the composition is free of non-contaminant Sn.

21. The antimicrobially acting phosphate glass composition according to claim 20, wherein the antimicrobially acting phosphate glass is usable in glass ceramics.

22. The antimicrobially acting phosphate glass composition according to claim 20, wherein the antimicrobially acting phosphate glass is usable in a glass powder or a glass ceramic powder.

23. The antimicrobially acting phosphate glass composition according to claim 22, wherein the glass powder or ceramic glass powder has particles having a size, on average, less than 20 μm.

24. An antimicrobially acting phosphate glass composition comprising, in weight percent on an oxide basis:
between greater than 45 and less than or equal to 90 of $P_2O_5$;
0 to 55 of $B_2O_3$;
0 to 40 of $SiO_2$;
less than 1 of $Al_2O_3$;
0 to 30 of $SO_3$;
0 to 0.1 of $Li_2O$;
0 to 0.1 of $Na_2O$;
0 to 0.1 of $K_2O$;
0 to 40 of CaO;
0 to 40 of MgO;
0 to 15 of SrO;
0 to 40 of BaO;
0 to 40 of ZnO;
0 to 5 of $Ag_2O$;
0 to 15 of CuO;
0 to 10 of $Cr_2O_3$;
0 to 10 of I;
0 to 10 of $TeO_2$;
0 to 10 of $GeO_2$;
0 to 10 of $TiO_2$;
0 to 10 of $ZrO_2$;
0 to 10 of $La_2O_3$;
0 to 5 of $Nb_2O_3$;
0 to 5 of $CeO_2$;
0 to 5 of $Fe_2O_3$;
0 to 5 of $WO_3$;
0 to 5 of $Bi_2O_3$; and
0 to 5 of $MoO_3$,
wherein a first sum formed from the $TiO_2$, the $ZrO_2$, the $BaO$, the $La_2O_3$, the $Cr_2O_3$, and the $Nb_2O_3$ lies in a range of 0.01 to 40 weight percent on oxide basis, wherein a second sum formed from the $Ag_2O$, the $ZnO$, the $CuO$, the $Cr_2O_3$, the I, the $TeO_2$, and the $GeO_2$ lies in a range of 0.1 to 40 weight percent on oxide basis, and wherein the composition is free of non-contaminant Sn.

25. The antimicrobially acting phosphate glass composition according to claim 24, wherein the antimicrobially acting phosphate glass is usable in glass ceramics.

26. The antimicrobially acting phosphate glass composition according to claim 24, wherein the antimicrobially acting phosphate glass is usable in a glass powder or a glass ceramic powder.

27. The antimicrobially acting phosphate glass composition according to claim 26, wherein the glass powder or ceramic glass powder has particles having a size, on average, less than 20 μm.

* * * * *